United States Patent [19]

Sorochenko

[11] Patent Number: 4,637,392

[45] Date of Patent: Jan. 20, 1987

[54] BIPOLAR ELECTROCOAGULATOR
[75] Inventor: Oleg A. Sorochenko, Kharkov, U.S.S.R.
[73] Assignee: Kharkovsky Nauchno-Issledovatelsky Institut Obschei i Neotlozhnoi Khirurgii, Kharkov, U.S.S.R.
[21] Appl. No.: 773,006
[22] Filed: Aug. 19, 1985
[51] Int. Cl.[4] .............................................. A61B 17/36
[52] U.S. Cl. ............................ 128/303.13; 128/303.17
[58] Field of Search ............ 128/303.1, 303.13, 303.17

[56] References Cited
U.S. PATENT DOCUMENTS
164,184 6/1875 Kidder ........................... 128/303.17

FOREIGN PATENT DOCUMENTS
2060397 5/1981 United Kingdom .
2064082 6/1981 United Kingdom .

OTHER PUBLICATIONS
"Surgical Diathermy in the Treatment of Cervicitis with a New Type of Flexible Spiral Electrode", Kimble, M. D., *Archives of Physical Therapy, X-Ray, Radium,* Feb. 1933, vol. IX, pp. 83–85.
Pasynkov, Y. I., General Physiotherapy, Moscow, Medgiz Publishers, 1962.
Instruments, Appareils et Materiel Medicaux, catalogue, vol. 2, 1961.

Primary Examiner—Kyle L. Howell
Assistant Examiner—Randy Citrin
Attorney, Agent, or Firm—Fleit, Jacobson, Cohn & Price

[57] ABSTRACT

A bipolar electrocoagulator comprises a working portion made as a body (1) of revolution interconnected with a drive (10), and one or two electrodes (2, 3) affixed on the surface of revolution of the body (1) to form a helix. The electrodes (2, 3) are connected, via current leads (5, 6) to a power source (12).

15 Claims, 9 Drawing Figures

BIPOLAR ELECTROCOAGULATOR

TECHNICAL FIELD

The present invention relates generally to surgical instruments and more specifically, to bipolar electrocoagulators.

BACKGROUND ART

Known in the art is a bipolar biactive electrocoagulator, comprising a cylinder one of whose end faces carries two electrodes, a flat end face of said cylinder serving as the working portion of such an electrocoagulator. A power source is connected to the electrodes through current leads, which feeds a radio-frequency current flowing between the electrodes through portions of living tissue during surgery (cf., e.g., "General Physiotherapy" by Ye. I. Pasynkov, Moscow, Medgiz Publishers, 1962 (in Russian).

Such an electrocoagulator features too a small effective area in contact with the tissues being operated, whereby to apply a hemostatic effect to a rather large area requires a prolonged length of time. This, in turn, extends operating time and causes heavy blood loss. Moreover, carbon deposit on the electrodes affects adversely the intensity of an r.f. electrical field so that blood coagulation ceases.

To restore normal operation of the instrument rather frequent cleaning of the electrodes from carbon deposit is required.

In addition, the aforementioned coagulator is inapplicable for producing hemostasis in hard-of-access places of human body, such as "pockets" or "pouches", ducts, depressions, caves, and some other structures in patients' living tissue.

Known in the art are also bipolar monoactive electrocoagulators, each comprising two electrodes of which one is shaped as a plate and the other, as a segment. Both of the electrodes are connected to an r.f. voltage source (cf., e.g., a catalogue "Medical instruments, apparatus, devices and equipment", Book 2, 1961).

DISCLOSURE OF THE INVENTION

The principal object of the invention is the provision of a bipolar electrocoagulator which would be applicable in hard-of-access operable places of a patient's body due to an efficient coagulate withdrawal from the operative wound.

The aforesaid object is accomplished due to the fact that in a bipolar electrocoagulator, comprising a working portion on which one or two electrodes are affixed which are connected, via current leads, to a power source, according to the invention, the working portion is shaped as a body of revolution interconnected with a power actuator, while the electrodes are secured on the surface of revolution of said body to form a helix.

The electrodes may have their cross-section shaped approximately as a semioval to reduce traumatic effect upon patient's tissues.

It is expedient that when a single electrode is provided on the coagulator working portion, a helical groove or flute be made on the surface of the body of revolution and the electrode be arranged flush with the fillets formed by the flute, and when two electrodes are provided on said coagulator working portion, both of them are reasonable to be made flush with the same flute fillet.

The body of revolution may be metallic, and the electrode be insulated therefrom.

It is also favourable that a double-start helical flute be provided on the surface of the body of revolution, and that each of the electrodes be located on the respective fillet of the flute.

It is highly advantageous that the body of revolution be metallic and serve as one of the electrodes, and that the other electrode located on the fillet of the helical flute be insulated.

A cone or ellipsoid is expedient to be used as the shape of the body of revolution.

The electrocoagulator is convenient to incorporate a device for its cleaning during surgery, said device being located in a close vicinity to the surface of the body of revolution.

BRIEF DESCRIPTION OF THE DRAWINGS

In what follows the present invention will now be disclosed in a detailed description of an illustrative embodiment thereof with reference to the accompanying drawings, wherein.

BEST MODE OF CARRYING OUT THE INVENTION

Figure 1:
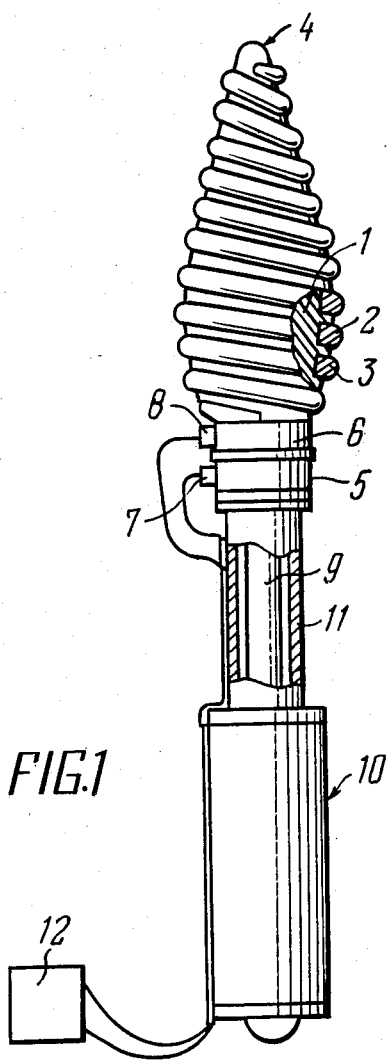
FIG. 1 is a bipolar electrocoagulator, according to the invention.

The bipolar electrocoagulator comprises a working portion made as a body 1 (FIG. 1) of revolution, one or two electrodes 2 and 3 being affixed on the surface of revolution of said body. The body of revolution may be an ellipsoid as in FIG. 1, or a cone (FIG. 2), or any similarly shaped body. The electrodes 2 and 3 (FIG. 1) are so arranged as to form a helix, viz., a single-start when use is made of one electrode, or a double-start when two electrodes are made use of.

An end 4 of the body 1 of revolution is rounded-off, while the other end carries current collectors 5 and 6, each of which is in contact with a respective current lead 7 or 8. The body 1 is connected to an electric drive 10 through a shaft 9. The shaft 9 is enclosed in a casing 11 rigidly held to the electric drive 10.

With a view to reducing traumatic effect during surgery the electrodes 2 and 3 have their cross-section shaped approximately as a semioval and are situated in depressions provided in the body 1 for the purpose.

The current leads 7 and 8 are connected to a power source 12 which may be in fact any r.f. voltage source of the known type. For example, a small power transformer which has a voltage of 27 volts, can be used which has a coagulation frequency of up to 1750 kHz, can cause a voltage across electrodes 2 and 3 up to 100 volts, has a high-frequency current up to 1.0 A, and can work at a speed from 150 to 200 revolutions per minute.

Figure 3:
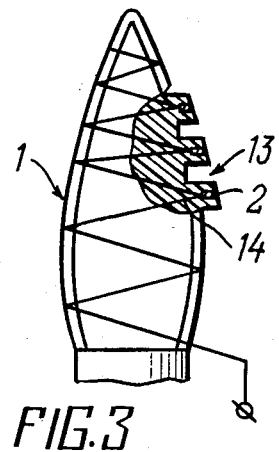
FIG. 3 is a partly sectional view of an electrocoagulator showing its working portion having a helical flute, according to the invention.
Figure 5:
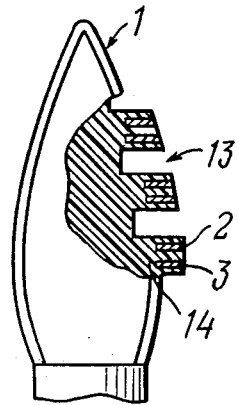
FIG. 5 is a fragmentary view of the body of revolution showing an embodiment, wherein two electrodes are provided in a bipolar biactive electrocoagulator, according to the invention.

A helical flute 13 may be provided on the surface of the body 1 of revolution as illustrated in FIG. 3. In this case the electrode 2 is located on fillets 14 (FIG. 3 or 4) if the electrocoagulator has a single electrode. When two electrodes are made use of both of them (2 and 3) are also situated on the fillets 14 (FIG. 5) flush with the latter.

Figure 4:
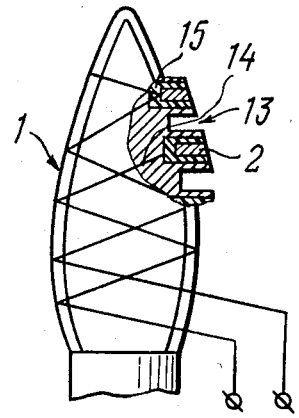
FIG. 4 is a fragmentary view of the metallic body of revolution presenting an embodiment, whereby a single electrode is provided in a bipolar monoactive electrocoagulator, according to the invention.
Figure 6:
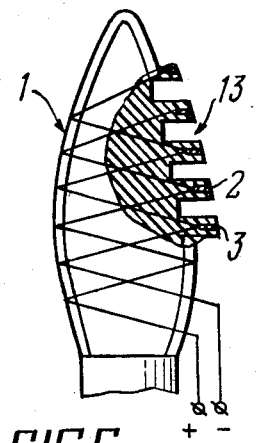
FIG. 6 is a view of FIG. 5 with a double-start helix, according to the invention.

The body 1 of revolution is most frequently made from plastics (FIG. 3 or 5), though it proves to be advantageous that the body be metallic (FIG. 4) with the electrodes 2 and 3 being isolated therefrom with an insulation layer 15. FIGS. 4 and 6 illustrate a double-start helix, the electrodes 2 and 3 being situated either on the same fillet (FIG. 5) or on different fillets (FIG. 6).

Figure 7:
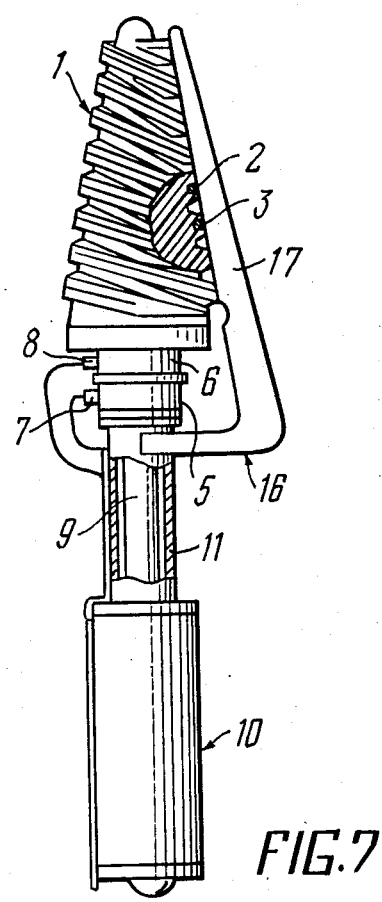
FIG. 7 is the same electrocoagulator incorporating a device for its cleaning, according to the invention.

A device 16 (FIG. 7) is provided in the coagulator for its cleaning purposes, said device being made fast close to the surface of the body 1 of revolution. The device 16 comprises a scraper 17 fixed stationary on the casing 11, while the working lip of the scraper is arranged parallel to the generator of the body 1 of revolution.

When the body 1 of revolution is metallic it becomes reasonable from technological viewpoint that body be at the same time one of the electrodes. According to such an embodiment the helical flute 13 provided on the body 1 and having the electrodes 2 and 3 located on the fillets 14 of said flute, forms an auger along which the coagulation products are traversable.

The bipolar coagulator discussed herein operates as follows.

With the electric drive 10 engaged rotation is transmitted, via the shaft 9, to the body 1 of revolution which is thus set in rotation along with the electrodes 2 and 3. An r.f. current is fed from the current leads 7 and 8 to the collectors 5 and 6 connected to the electrodes 2 and 3.

Figure 2:
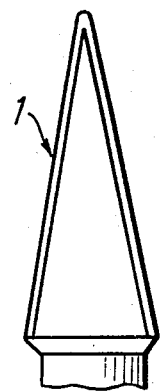
FIG. 2 is a working portion of the electrocoagulator shaped as a cone, according to the invention.

An r.f. current field built up between the electrodes 2 and 3 upon introducing the body 1 into the operative wound, turns blood into coagulate while fusing the blood and lymph vessels. The resultant coagulate gets into the helical flute established on the body 1 by the helix, and is withdrawn from the operative wound axially towards the holder formed by the casing 11 and the drive 10 (FIG. 1).

The electrodes 2 and 3 get in contact with the coagulated consolidated tissue, thus becoming self-cleaned due to the forces of friction. The coagulate remaining on the surface of the electrodes is cleansed by the scraper 17 and is discarded into the helical flute to be withdrawn from the operative wound. Thus, the coagulate is removed from the operative wound along a specially provided nonelectrically conductive helical flute rather than by virtue of the electrodes 2 and 3 themselves.

Figure 8A:
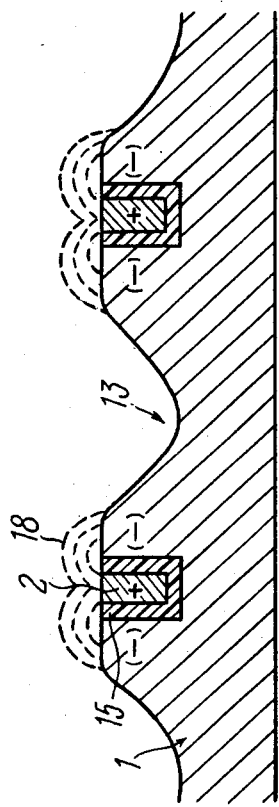
FIGS. 8a, b represents a graphic chart showing current propagation in living tissues observed during electrocoagular application.
Figure 8B:
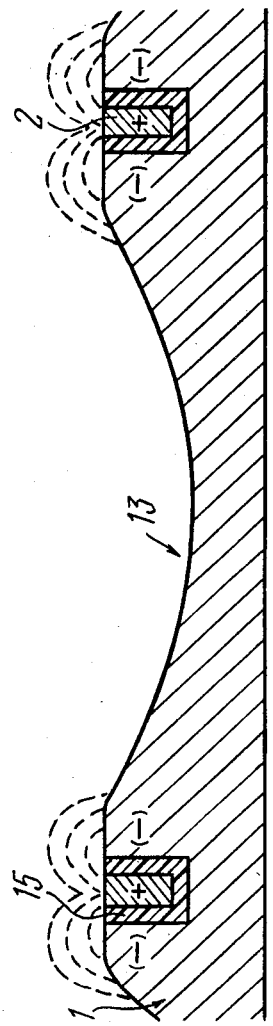

In addition, no carbon deposit is formed on the electrode surfaces since current does not propagate other than along the surface of the tissue being coagulated, which is clearly evident from FIGS. 8a and b, wherein a graphic chart representing current propagation in living tissues with use of the present electrocoagulator is illustrated.

The graphic chart refers to an embodiment of the invention, wherein the body 1 of revolution is metallic and illustrates the distribution of lines 18 of force of a field induced by the current flowing along the electrode 2. The distribution of the lines 18 of force remains invariable when the width of the flute 13 is changed, that is, it does not depend upon variation in the interturn spacing of the helix. The direction of current flow in FIGS. 8a and b at a given instant is conventionally indicated with the sign "+" (towards the observer) or "—" (away from the observer).

All the above-discussed improves the operating conditions of the electrocoagulator and facilitates its self-cleaning.

Considered below is the operation of an electrocoagulator, wherein the body 1 (FIG. 4) serves as one of the electrodes.

When the drive 10 is engaged rotation is imparted, via the shaft 9, to the body 1 which rotates together with the electrode 2. R.f. current is fed from the source 12 via the current leads 7 and 8 to the collectors 5 and 6, and further on to the electrode 2. As a result, an r.f. current field is established between the turns of the helical flute 13 and the adjacent active portions 18 (19) (FIGS. 8a, b) of the electrode 2, said field being concentrated at the fillets 14, while being practically absent between the fillets. Upon introducing the body 1 into the operative wound current flows between the active portions 18, 19 of the electrodes, thus turning the blood into coagulate and fusing the blood and lymph vessels in the wound.

The resultant coagulate and blood clots get into the helical flute 13 and are carried away from the operative wound axially towards the casing 11. The fillets 14, while contacting the coagulated consolidated tissue, are self-cleaned by virtue of the forces of friction. The residual coagulate is removed by the scraper 17 and discarded into the helical flute 13 to be withdrawn from the operative wound.

The aforedescribed embodiment of the coagulator, wherein the metallic body of revolution serves at the same time as one of the electrodes is advantageous in that it dispenses with a double-start coiling of two electrodes at a time, which requires strict observance of a preset spacing between adjacent turns of the unlike-polarity electrodes. Thus, the width of the helical flute can be increased which enables much larger amounts of coagulates and blood clots to be conveyed per unit time, making it possible to cleanse badly bleeding operative wounds.

Another advantageous feature of the aforedescribed construction resides in intense extraction of heat that evolves in the course of surgery, thus attaining more profound and quality tissue coagulation and preventing coagulate from sticking to the electrode working surfaces. This in turn renders the operation of the electrocoagulator as a whole more reliable.

The instrument is simple to manufacture and features small overall dimensions.

Industrial Applicability

The invention can find application for surgery on the parenchymatous organs or soft tissues with a view to arresting hemorrhage in urgent and preplanned surgery, for cleansing ducts, fissures, "pockets" or "pouches" and large areas in primary infected wounds. The invention is also applicable in oncosurgery for performing major surgical procedures, in neurosurgery, vascular surgery, as well as in surgery on the gastrointestinal tract.

I claim:

1. A bipolar electrical coagulator comprising:
   a working body of revolution which is introduced into a wound during surgery, said working body of revolution having a peripheral surface;
   a first electrode secured to said peripheral surface forming a helix and a groove;
   a second electrode on the body of revolution;
   electrical leads connected to each of said first and second electrodes;
   a first current collector disposed on said working body of revolution which is electrically connected to said first electrode;
   a second current collector disposed on said working body of revolution which is electrically connected to said second electrode;
   an electrical power supply connected to said first and second current collectors, whereby an electric field is built up between said first electrode and said second electrode to cause blood to coagulate and form coagulant; and
   an electric drive means connected to said working body of revolution for causing said working body of revolution and said first and said second electrodes to rotate and remove said coagulant by means of said helix into said groove.

2. The biopolar electrical coagulator according to claim 1 wherein said second electrode is secured to said peripheral surface to form a second helix; and
   further comprising a two-start helix formed by the helix formed by said first electrode and said second helix, said two-start helix having a helical groove located between said first electrode and said second electrode for removing said coagulant.

3. The bipolar electric coagulator according to claim 2, wherein said first electrode and said second electrode each has a half-oval cross-sectional configuration.

4. The bipolar electric coagulator according to claim 1 wherein said groove is provided on said peripheral surface to define a fillet on said surface; and wherein said first electrode is secured to, and flush with said fillet.

5. The bipolar electric coagulator according to claim 4, wherein said working body of revolution is made of metal and wherein said working body of revolution further comprises an electrical insulation layer insulating said first electrode from said working body of revolution.

6. The bipolar electric coagulator according to claim 2, wherein said working body of revolution is made of metal and wherein said working body of revolution further comprises an electrical insulation layer insulating said first electrode and said second electrode from said working body of revolution.

7. The bipolar electric coagulator according to claim 2, wherein said helical groove is provided on said peripheral surface to define fillets on said peripheral surface; and wherein said first and second electrodes are secured to and flush with said fillets.

8. The bipolar electric coagulator according to claim 2, wherein a two-start helical groove is provided on said peripheral surface to define a first row of fillets and a second row of fillets extending along a helical line; and wherein
   said first electrode is secured to, and flush with said first row of fillets, and said second electrode is secured to, and flush with said second row of fillets.

9. The bipolar electric coagulator according to claim 1, wherein a helical groove is provided on said peripheral surface to define fillets on said peripheral surface;
   a layer of electrical insulation is provided on said fillets;
   said first electrode is secured to, and flush with said layer of electrical insulation;
   said working body of revolution is made of metal and defines a second electrode; and wherein
   said second current collector is electrically connected to said working body of revolution.

10. The bipolar electric coagulator according to claim 1, wherein the shape of said working body of revolution is the form of a cone.

11. The bipolar electric coagulator according to claim 1, wherein the shape of said working body of revolution is in the form of an ellipsoid.

12. The bipolar electric coagulator according to claim 2, wherein the shape of said working body of revolution is in the form of a cone.

13. The bipolar electric coagulator according to claim 2, wherein the shape of said working body of revolution is in the form of an ellipsoid.

14. The bipolar electric coagulator according to claim 1, further comprising a cleansing means for cleansing said electric coagulator during surgery, and wherein, said cleansing means is secured in close proximity to said peripheral surface.

15. A bipolar coagulator comprising:
    a working body of revolution which is introduced into a wound during surgery, said working body of revolution having a peripheral surface;
    a helical groove disposed on said peripheral surface to define fillets;
    a first electrode which is secured to and flush with said fillets along a helical line;
    a second electrode which is secured to and flush with said fillets along a helical line;
    electrical leads connected to said first and second electrodes;
    a first current collector disposed on said working body of revolution which is electrically connected to said first electrode;
    a second current collector disposed on said working body of revolution which is electrically connected to said second electrode;
    a power supply source connected to said first and second current collectors, whereby an electric field is built up between said first and said second electrode to cause blood to coagulate and form coagulant; and
    an electric drive means connected to said working body of revolution for causing said working body of revolution, said helical groove and said first and second electrodes to rotate and remove said coagulant by means of said helix into said groove.

* * * * *